United States Patent
Krüger et al.

[11] Patent Number: 6,147,091
[45] Date of Patent: Nov. 14, 2000

[54] ARTHROPOD REPELLANT

[75] Inventors: Bernd-Wieland Krüger, Bergisch Gladbach; Günther Nentwig; Klaus Röder, both of Leverkusen, all of Germany

[73] Assignee: Bayer Aktiengesellschaft, Leverkusen, Germany

[21] Appl. No.: 09/180,067

[22] PCT Filed: Apr. 25, 1997

[86] PCT No.: PCT/EP97/02138

§ 371 Date: Oct. 30, 1998

§ 102(e) Date: Oct. 30, 1998

[87] PCT Pub. No.: WO97/41728

PCT Pub. Date: Nov. 13, 1997

[30] Foreign Application Priority Data

May 6, 1996 [DE] Germany ............... 196 18 089

[51] Int. Cl.$^7$ .......... A01N 43/40; A01N 37/02; A01N 37/06; A01N 37/00
[52] U.S. Cl. .......... 514/315; 514/546; 514/547; 514/549; 514/552; 514/557; 514/558; 514/560; 514/786; 514/919; 424/195.1; 424/DIG. 10
[58] Field of Search .................. 514/315, 919, 514/546, 547, 549, 552, 557, 558, 560, 786; 424/195.1, DIG. 10

[56] References Cited

U.S. PATENT DOCUMENTS

| | | | |
|---|---|---|---|
| 4,873,252 | 10/1989 | Krüger et al. | 514/315 |
| 4,900,834 | 2/1990 | Krüger et al. | 546/245 |
| 4,946,850 | 8/1990 | Krüger et al. | 514/315 |
| 5,008,261 | 4/1991 | Krüger et al. | 514/212 |
| 5,589,181 | 12/1996 | Bencsits | 424/405 |

FOREIGN PATENT DOCUMENTS

| | | |
|---|---|---|
| 0 289 842 A1 | 1/1988 | European Pat. Off. |
| 38 42 323 A1 | 6/1990 | Germany |
| WO 93/16594 | 9/1993 | WIPO |

OTHER PUBLICATIONS

Chemical Abstracts 121:224313, 1994.
Chemical Abstracts 122:154200, 1995.
Chemical Abstracts 124:155686, 1996.
Chemical Abstracts 124:310201, 1996.
Abstract of JP 04244001–A, Taisho Pharm Co., Ltd., Jun. 18,1990.
Database WPI, Section Ch, Week 8315, Derwent Publications Ltd., London, GB;, AN 83–36013K, JP 58 039 603 A, Mar. 3, 1983.
K.H. Buchel, Chemie der Pflanzenschutz–und Schadlingsbekampfungsmittel (Chemistry of Crop Protection Products and Pesticides); Edition: R. Wegler, vol. 1, Springer Verlag Berlin Heidelberg, New York, 1970, p. 487 et seq.)

*Primary Examiner*—John Pak
*Attorney, Agent, or Firm*—Norris, McLaughlin & Marcus, P.A.

[57] ABSTRACT

The present invention relates to compositions for repelling arthropods, these compositions being based on piperidine derivatives of the formula (I)

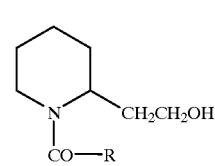

in which R represents alkyl or alkoxy, together with fatty acids and/or fatty acid derivatives as synergists.

11 Claims, 1 Drawing Sheet

ARTHROPOD REPELLANT

This application is a 371 of PCT/EP97/02138, filed on Apr. 25, 1997.

The present invention relates to compositions for repelling arthropods, these compositions being based on piperidine derivatives and fatty acids and fatty acid derivatives as synergists.

It has been disclosed that certain piperidine derivatives can be employed as agents for repelling insects and mites (cf. EP-A 0 281 908 and EP-A 0 289 842). However, a considerable disadvantage of the known repellents is their long-term action, which is relatively short in some cases.

A considerable disadvantage of the known repellents is their long-term action, which is relatively short in some cases.

The prolonged activity of certain repellents, for example Deet®, due to a combination with vegetable oils and/or fatty acids and/or their esters has also been disclosed (cf., for example, DE-A 38 42 232 and JP 042 44 001). Again, the long-term action of these mixtures is not always satisfactory.

It has been found that mixtures of piperidine derivatives of the formula (I)

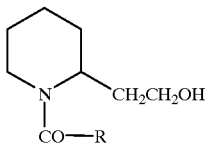
(I)

in which
R represents alkyl or alkoxy
with fatty acids and/or fatty acid derivatives as synergists have good arthropod-repellent properties.

The repellent action of the mixtures according to the invention is considerably more potent than that of the pure piperidine derivatives, the fatty acids causing not only an additive, but a synergistic, increase in activity.

The compositions according to the invention are therefore a valuable enrichment of the art.

Formula (I) provides a general definition of the piperidine derivatives. Preferred compounds are those in which R represents $C_1$–$C_4$-alkyl or $C_1$–$C_4$-alkoxy. Especially preferred compounds are those in which R represents $C_3$–$C_4$-alkyl or $C_3$–$C_4$-alkoxy.

Very especially preferred compounds of the formula (I) which can be used according to the invention are the following:

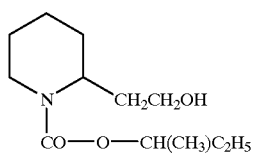
(I-1)

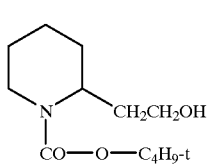
(I-2)

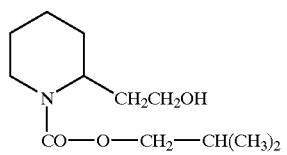
(I-3)

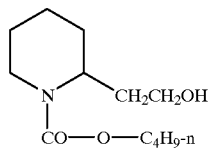
(I-4)

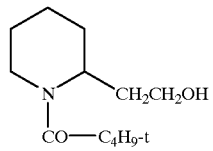
(I-5)

The piperidine derivatives which can be used according to the invention have been disclosed (cf. EP-A 0 281 908 and EP-A 0 289 842).

Synergists which are suitable for the mixtures according to the invention are preferably even-numbered, straight-chain higher fatty acids, in particular $C_6$–$C_{18}$-fatty acids, or their derivatives such as, in particular, fatty acid esters.

Synergists which may especially preferably be mentioned are caprylic acid ($C_8$) and capric acid ($C_{10}$) and their alkyl esters such as, in particular, the methyl esters.

The fatty acids or their derivatives can be employed singly or in the form of variously composed mixtures of a variety of fatty acids/fatty acid derivatives.

It is also possible to employ substances which contain a mixture of various fatty acids in the first place, such as, preferably, vegetable oils.

Examples which may be mentioned are: citronella oil, clove oil, patchouli oil, rapeseed oil, juniper oil or coconut oil.

The compositions of the inventive mixtures of compounds of formula (I) and fatty acids and/or fatty acid derivatives can vary within a substantial range. Preferably the mixtures contain 1 to 90 percent per weight, more preferred 1 to 50 percent per weight and especially preferred 1 to 20 percent per weight of components of formula (I).

In a special embodiment, the mixtures according to the invention of piperidine derivatives of the formula (I) with fatty acids or fatty acid derivatives as synergists may also comprise other arthropod repellents. All repellents which can conventionally be used may be employed (cf., for example, K. H. Büchel, Chemie der Pflanzenschutz-und Schädlingsbekampfungsmittel [Chemistry of Crop Protection Products and Pesticides]; Editor: R. Wegler, Vol. 1, Springer Verlag Berlin Heidelberg New York, 1970, p. 487 et seq.).

Substances which are preferably used are repellent carboxamides, 1,3-alkanediols, carboxylates, lactone derivatives and also β-alanine derivatives which are disubstituted on the nitrogen. Individual examples which may be mentioned are: N,N-diethyl-3-methylbenzamide (Deet), N,N-diethylphenylacetamide (DEPA), 2-ethyl-hexane-1,3-diol (Rutgers 612), dimethyl phthalate, 1,1,4,5,6,7,8,8a-octahydro-3H-2-benzopyran-3-one and ethyl 3-(N-n-butyl-N-acetyl)-aminopropionate.

The mixtures according to the invention can be used successfully for repelling sucking and biting arthropods which are harmful or a nuisance, preferably insects, ticks and mites.

The sucking insects include essentially the mosquitoes (for example *Aedes aegypti, Aedes vexans, Culex quinquefasciatus, Culex tarsalis, Anopheles albimanus, Anopheles gambiae, Anopheles stephensi, Mansonia titillans*), moth gnats (for example *Phlebotomus papatasii*), gnats (for example *Culicoides furens*), buffalo gnats (for example *Simulium damnosum*), biting flies (for example *Stomoxys calcitrans*), tsetse flies (for example *Glossina morsitans morsitans*), horse flies (for example *Tabanus nigrovittatus, Haematopota pluvialis, Chrysops caecutiens*), true flies (for example *Musca domestica, Musca autumnalis, Musca vetustissima, Fannia canicularis*), flesh-flies (for example *Sarcophaga carnaria*), myiasis-causing flies (for example *Lucilia cuprina, Chrysomyia chloropyga, Hypoderma bovis, Hypoderma lineatum, Dermatobia hominis, Oestrus ovis, Gasterophilus intestinalis, Cochliomyia hominivorax*), bugs (for example *Cimex lectularius, Rhodnius prolixus, Triatoma infestans*), lice (for example *Pediculus humanis, Haematopinus suis, Damalina ovis*), fleas (for example *Pulex irritans, Xenopsylla cheopis, Ctenocephalides canis, Ctenocephalides felis*) and sand fleas (*Dermatophilus penetrans*).

The biting insects include essentially cockroaches (for example *Blattella germanica, Periplaneta americana, Blatta orientalis, Supella longipalpa*), beetles (for example *Sitiophilus granarius, Tenebrio molitor, Dermestes lardarius, Stegobium paniceum, Anobium punctatum, Hylotrupes bajulus*), termites (for example *Reticulitermes lucifugus*), ants (for example *Lasius niger, Monomorium pharaonis*), wasps (for example *Vespula germanica*) and larvae of moths (for example *Ephestia elutella, Ephestia cautella, Plodia interpunctella, Hofmannophila pseudospretella, Tineola bisselliella, Tinea pellionella, Trichophaga tapetzella*).

The remaining arthropods include ticks (for example *Ixodes ricinus, Argas reflexus, Ornithodorus moubata, Boophilius microplus, Amblyomma hebraeum*) and mites (for example *Sarcoptes scabiei, Dermatophagoides pteronyssinus, Dermatophagoides farinae, Dermanyssus gallinae, Acarus siro*).

The mixtures according to the invention, which can be employed undiluted or, preferably, diluted, may be employed in the formulations conventionally used for repellents.

For use on humans or animals, these are solutions, emulsions, gels, ointments, pastes, soaps, shampoos, creams, powders, sticks, impregnated sponges, microcapsules, sprays or aerosols from spray cans.

A possible formulation for mixtures according to the invention specifically in the field of veterinary medicine is polymeric shaped articles (for example ear tags, collars, medallions).

For use in or outside buildings, the mixtures according to the invention can be incorporated into granules, oil sprays, organic and water-based concentrates or slow-release formulations.

Moreover, the mixtures according to the invention may be employed in vaporizer systems: The compounds are either located on a cellulose tablet resting on a plate which is heated electrically or by means of a flame, or they are in solution in a reservoir from which they are released into the atmosphere of the room by means of a heated wick. Instead of the cellulose tablet, it is also possible to use an aluminium trough, sealed with a membrane, which contains the compounds in the form of a gel.

Furthermore, the mixtures according to the invention may be formulated as mosquito coils or candles, where burning makes the substances evaporate from the burning site.

The products are prepared in a known manner by mixing or diluting the mixtures according to the invention with solvents (for example xylene, chlorobenzenes, paraffins, methanol, ethanol, isopropanol, water), carriers (for example kaolins, clays, talc, chalk, highly-disperse silica, silicates), emulsifiers (for example polyoxyethylene fatty acid esters, polyoxyethylene fatty alcohol ethers, alkylsulfonates, arylsulfonates) and dispersants (for example lignin-sulfate waste liquors, methyl cellulose) or by incorporation in microcapsules (for example based on gum arabic, gelatin, urea).

The mixtures according to the invention are employed in any desired ratio and can be used, in the formulations, as a mixture with each other or else as a mixture with other known active compounds (for example sunscreens). In general, the preparations comprise between 0.1 and 95% by weight, preferably between 0.5 and 90% by weight, of mixture according to the invention.

To afford protection against the abovementioned arthropods, the mixtures according to the invention are either applied to the human or animal skin or hair, or coat, respectively, or used to treat items of clothing and other objects.

The mixtures according to the invention are also suitable as a constituent of impregnants, for example for textile webs, curtains, items of clothing, packing materials, and for use in polishing materials, detergents and window cleaners.

The invention will be illustrated in greater detail by the following general examples for the preparations and the use of the mixtures according to the invention.

BRIEF DESCRIPTION OF THE DRAWINGS

The illustration of the invention in greater detail will make reference to the drawings, wherein.

FORMULATION EXAMPLE 1

Figure 1:
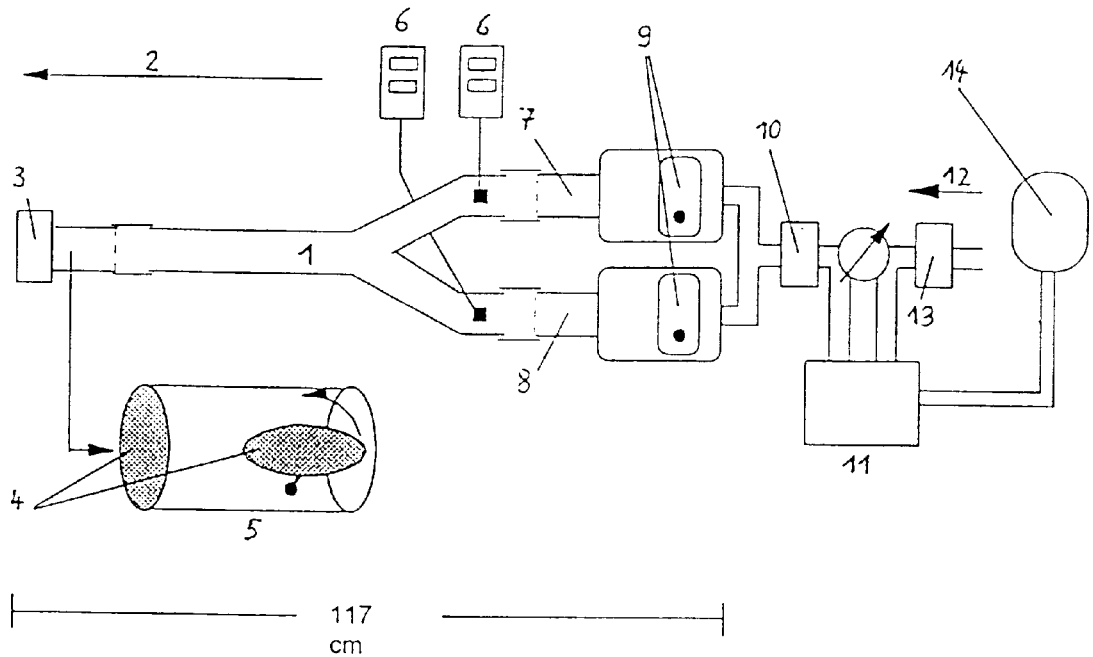
FIG. 1 is a drawing depicting a Y-olfactometer.

A repellent in the form of a lotion for use on human or animal skin is prepared by mixing 20 parts of one of the mixtures according to the invention, 1.5 parts of fragrance and 78.5 parts of isopropanol or ethanol.

FORMULATION EXAMPLE 2

A repellent in the form of an aerosol for spraying onto the human or animal skin is composed of 40% active compound solution (consisting of 20 parts of one of the mixtures according to the invention, 1 part of fragrance and 79 parts of isopropanol) and 60% of propane/butane (ratio 15:85).

USE EXAMPLES

The following are employed in the use examples below:
a) Pyridine derivative of the formula (I):

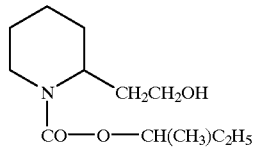

(I-1)

b) Synergist:
   $C_8$-fatty acid (caprylic acid) or
   $C_{10}$-fatty acid (caprinic acid) or
   $C_8/C_{10}$-fatty acid mixture, ratio 1:1

EXAMPLE A

As a repellent on the skin
Method:

Gauze cages of dimensions 50×60×60 cm contain midge populations (*Aedes aegypti*) of approximately 5,000 specimens of all ages and both sexes. The animals are fed exclusively on sugar-water.

A guinea pig whose back has been shorn the previous day over an area of 50 cm$^2$ and then treated with depilatory cream (cream was subsequently removed with water) is held in place in a cage (box) in such a way that only the shorn area is accessible for the mites.

After the area has been treated with 0.4 ml of preparation (mixture according to the invention in isopropanol) (using a pipette), the guinea pig, including box, is placed into a cage containing the test animals.

Observation over 5 minutes reveals the number of midges which have bitten the guinea pig. The latter is then removed, and the test is repeated after one hour. The experiment is carried out for not longer than 9 hours, or until the activity ceases (>5 bites).

3 replications are carried out per preparation, and, after the experiment has ended, the average is calculated for each evaluation time.

If the activity ceases earlier in one replication, the last value determined continues to be used for the evaluation times which follow and is included in the calculation of the averages of the subsequent evaluation times.

The synergism is detected using S. R. Colby's formula; Weeds 15 20–22:

$$E = X + Y - \frac{X \cdot Y}{100}$$

E=expected duration of protection of the mixture according to the invention
X=actual duration of protection of the pyridine derivative of the formula (I) alone
Y=actual duration of protection of the fatty acid(s) alone If E is less than the actually observed duration of protection of the mixture, then synergism is present.

Results:
Temperature: 25–27° C., relative atmospheric humidity: approx. 60%

TABLE 1

Compound of the formula (I-1) with $C_8/C_{10}$-fatty acid mixture; E = 5.95 hours

| Preparation | \multicolumn{10}{c}{Number of bites on the guinea pig after} | Duration of protection |
|---|---|---|---|---|---|---|---|---|---|---|---|
| | 0 h | 1 h | 2 h | 3 h | 4 h | 5 h | 6 h | 7 h | 8 h | 9 h | |
| 1% (I-1) 1% $C_8/C_{10}$ | 0 | 0 | 0 | 2.0 | 4.7 | 5.3 | | | | | 5 h |
| 1% (I-1) 2% $C_8/C_{10}$ | 0 | 0 | 0 | 1.0 | 4.0 | 4.0 | 4.0 | 4.3 | 4.0 | 5.7 | 9 h |
| 2% (I-1) 1% $C_8/C_{10}$ | 0 | 0.3 | 0.3 | 0 | 1.7 | 1.7 | 3.0 | 6.7 | | | 7 h |
| 2% (I-1) 2% $C_8/C_{10}$ | 0 | 0 | 0.3 | 0 | 0.7 | 1.3 | 3.3 | 4.3 | 4.3 | 5.3 | 9 h |
| 2% (I-1) without addition | 0.7 | 0 | 0.3 | 0.3 | 4.3 | 6.0 | | | | | 5 h |
| 2% $C_8/C_{10}$ alone | 0.5 | 8.5 | | | | | | | | | 1 h |

TABLE 2

Compound of the formula (I-1) with $C_8$-fatty acid; E = 5.00 hours

| Preparation | \multicolumn{8}{c}{Number of bites on the guinea pig after} | Duration of protection |
|---|---|---|---|---|---|---|---|---|---|
| | 0 h | 1 h | 2 h | 3 h | 4 h | 5 h | 6 h | 7 h | |
| 2% (I-1) 1% $C_8$ | 0 | 0.3 | 0.3 | 0.3 | 0.3 | 1.3 | 2.3 | 7.7 | 7 h |
| 2% (I-1) 2% $C_8$ | 0 | 0 | 0 | 1.0 | 2.3 | 4.7 | 4.7 | 6.3 | 7 h |
| 2% (I-1) without addition | 0 | 0 | 0.7 | 1.0 | 2.3 | 6.7 | | | 5 h |
| 2% $C_8$ alone | 7.0 | | | | | | | | 0 h |

TABLE 3

Compound of the formula (I-1) with $C_{10}$-fatty acid; E = 5.00 hours

| Preparation | \multicolumn{8}{c}{Number of bites on the guinea pig after} | Duration of protection |
|---|---|---|---|---|---|---|---|---|---|
| | 0 h | 1 h | 2 h | 3 h | 4 h | 5 h | 6 h | 7 h | |
| 2% (I-1) 1% $C_{10}$ | 0 | 0.3 | 0.3 | 1.0 | 3.3 | 4.7 | 6.3 | | 6 h |
| 2% (I-1) 2% $C_{10}$ | 0 | 0 | 0 | 0.3 | 1.0 | 3.7 | 3.7 | 8.3 | 7 h |
| 2% (I-1) without addition | 0 | 0 | 0.3 | 2.0 | 4.7 | 6.0 | | | 5 h |
| 2% $C_{10}$ alone | 8.0 | | | | | | | | 0 h |

EXAMPLE B

As a repellent in vaporizer systems
Method

The experiments are carried out in a Y-olfactometer as shown in FIG. 1:
FIG. 1
1=Y-tube
2=current (20–30 cm/s)/temperature 27–29° C./rel. humidity 70–80%

Figure 2:
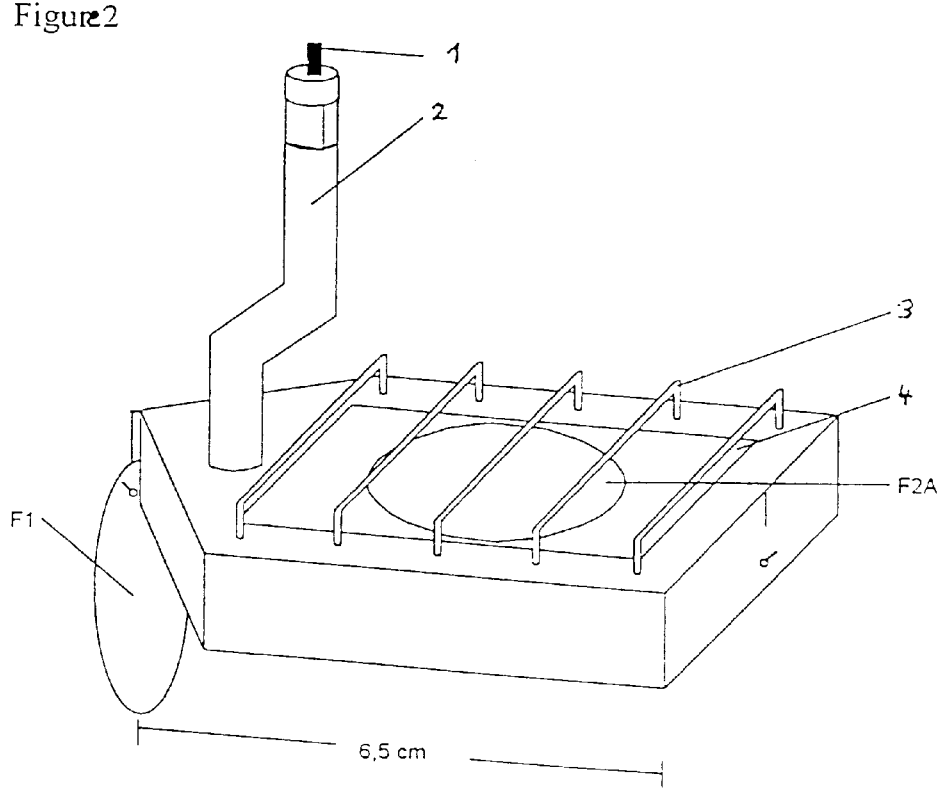
FIG. 2 is a heater unit used in the Y-olfactometer of FIG. 1.

3=fan
4=gauze
5=container (removable from Y-tube)
6=thermometer and detector for humidity
7=container K
8=container T
9=stimulation part
10=heater
11=water reservoir
12=compressed air
13=activated carbon
14=water supply A container containing 20–30 midges (*Aedes aegypti*) which have been lured into the container by hand from a cage is attached on the left-hand side of the olfactometer as can be seen in FIG. 1 (gauze-sealed). After the animals have been allowed to settle for 10 minutes, the stimulation port of container T is equipped with a small heater (plate temperature 110° C.) on which there are positioned, on filter paper, a skin extract (source of attractant stimulation) or 0.1 ml of preparation (mixture according to the invention in methanol)+skin extract (FIG. 2):

FIG. 2
1=cable
2=arrangement to be hung up in the olfactometer
3=fence
4=hotplate
F1=Filter disc with skin extract
F2A=Filter disc with preparation on hotplate After 1 minute, the containers are closed, the heater is removed, and the midges in the containers are counted.

The activity is calculated using the following formula:

$$\frac{(\text{No. in container } T) - (\text{No. in container } C{:}2) - (\text{No. outside})}{\text{Total}} \times 100$$

+100 denotes the highest attractant effect (all midges in container T), −100 means the highest repellent effect (all midges outside).

After the test, the midges are removed, and, after the olfactometer has been run empty for 10 minutes, fresh midges are introduced, which are again allowed to settle for 10 minutes.

A test series is started with skin extract, then the preparation+skin extract is tested, and finally again the skin extract.

The synergism is detected using the above-described formula of S. R. Colby; Weeds 15, 20–22.

Results:

Temperature: 26–28° C., relative atmospheric humidity: approx. 75%

TABLE 1

Compound of the formula (I-1) with $C_8/C_{10}$-fatty acid mixture; E = −51.96

| Preparation | | | Activity |
|---|---|---|---|
| | only | skin extract | +73 |
| 1.0 mg (I-1) 1.0 mg $C_8/C_{10}$ | + | skin extract | −73 |
| 1.0 mg (I-1) without addition | + | skin extract | −16 |
| 1.0 mg $C_8/C_{10}$ alone | + | skin extract | −31 |
| | only | skin extract | +93 |

TABLE 2

Compound of the formula (I-1) with $C_8$-fatty acid; E = +37.10

| Preparation | | | Activity |
|---|---|---|---|
| | only | skin extract | +87 |
| 1 mg (I-1) 1 mg $C_8$ | + | skin extract | −22 |
| 1 mg (I-1) without addition | + | skin extract | +26 |
| 1 mg $C_8$ alone | + | skin extract | +15 |
| | only | skin extract | +75 |

TABLE 3

Compound of the formula (I-1) with $C_{10}$-fatty acid; E = −24.32

| Preparation | | | Activity |
|---|---|---|---|
| | only | skin extract | +75 |
| 1 mg (I-1) 1 mg $C_{10}$ | + | skin extract | −85 |
| 1 mg (I-1) without addition | + | skin extract | +16 |
| 1 mg $C_{10}$ alone | + | skin extract | −48 |
| | only | skin extract | +73 |

What is claimed is:

1. An arthropod repellent composition comprising a combination of at least one piperidine derivative of the formula (I):

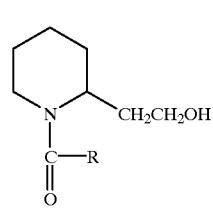

(I)

in which

R represents alkyl or alkoxy, and at least one fatty acid and/or fatty acid ester.

2. The arthropod repellant composition according to claim 1, wherein R in formula (I) represents $C_1$–$C_4$-alkyl or $C_1$–$C_4$-alkoxy.

3. The arthropod repellant composition according to claim 1, which comprises at least one piperidine derivative of the formulae:

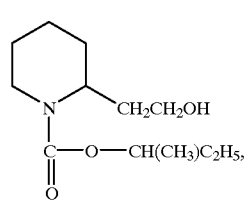

(I-1)

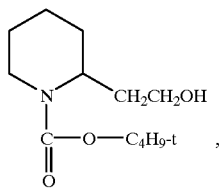
(I-2)

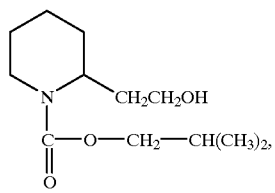
(I-3)

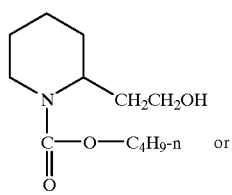
(I-4)

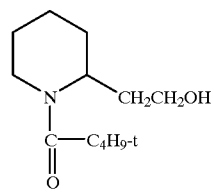
(I-5)

and at least one fatty acid and/or fatty acid ester.

4. The arthropod repellant composition according to claim 1, wherein the fatty acid and/or fatty acid ester is selected from the group consisting of even-numbered, straight-chain $C_6$–$C_{18}$ fatty acids and their esters.

5. The arthropod repellant composition according to claim 4, wherein the fatty acid and/or fatty acid ester is selected from the group consisting of caprylic acid ($C_8$), capric acid ($C_{10}$) and their alkyl esters.

6. The arthropod repellant composition according to claim 5, wherein the fatty acid ester is methyl caprate.

7. The arthropod repellant composition according to claim 1, wherein the fatty acid and/or fatty acid ester is a mixture of fatty acids.

8. The arthropod repellant composition according to claim 1, wherein the fatty acid ester is in the form of at least one vegetable oil.

9. The arthropod repellant composition according to claim 8, wherein the vegetable oil is selected from the group consisting of citronella oil, clove oil, patchouli oil, rapeseed oil and juniper oil.

10. The arthropod repellant composition according to claim 1, wherein the combination of the piperidine derivative of formula (I) and the fatty acid and/or fatty acid ester comprises between 0.1 and 95% by weight of the arthropod repellant composition.

11. A process for repelling arthropods, said process comprising applying to said arthropods or to an area from which it is desired to exclude said arthropods an arthropod repelling effective amount of an arthropod repellant composition according to any one of claims 1–10.

* * * * *

UNITED STATES PATENT AND TRADEMARK OFFICE
CERTIFICATE OF CORRECTION

PATENT NO. : 6,147,091  
DATED : November 14, 2000  
INVENTOR(S) : Kruger et al.

It is certified that error appears in the above-identified patent and that said Letters Patent is hereby corrected as shown below:

<u>Title page,</u>  
References Cited, FOREIGN PATENT DOCUMENTS,  
Line 4, delete "38 42 323 A1" and substitute -- 38 42 232 A1 --

<u>Column 10,</u>  
Line 15, delete "misture" and substitute -- mixture --

Signed and Sealed this

Twenty-sixth Day of February, 2002

Attest:

JAMES E. ROGAN  
*Attesting Officer*  *Director of the United States Patent and Trademark Office*